(12) United States Patent
Tsaur et al.

(10) Patent No.: US 11,096,959 B2
(45) Date of Patent: Aug. 24, 2021

(54) MICROENVIRONMENT HYDROGEN-SUPPLYING BREATHABLE LAYER AND APPLICATIONS THEREOF

(71) Applicant: TO2M CORPORATION, Hsinchu (TW)

(72) Inventors: Garry Tsaur, Rowland Heights, CA (US); Ting-Hua Wang, Rowland Heights, CA (US); Frank Tsaur, Rowland Heights, CA (US); Nancy Tsaur, Rowland Heights, CA (US); Emily Tsaur, Rowland Heights, CA (US)

(73) Assignee: TO2M CORPORATION, Hsinchu (TW)

( * ) Notice: Subject to any disclaimer, the term of this patent is extended or adjusted under 35 U.S.C. 154(b) by 237 days.

(21) Appl. No.: 16/432,055

(22) Filed: Jun. 5, 2019

(65) Prior Publication Data
US 2020/0237807 A1   Jul. 30, 2020

(30) Foreign Application Priority Data
Jan. 25, 2019   (TW) .................................. 108102849

(51) Int. Cl.
| | |
|---|---|
| *A61F 13/00* | (2006.01) |
| *A61K 33/00* | (2006.01) |
| *A61M 35/00* | (2006.01) |
| *A61F 13/84* | (2006.01) |
| *C01B 3/06* | (2006.01) |
| *A61F 5/30* | (2006.01) |
| *A61F 13/14* | (2006.01) |
| *C01B 13/02* | (2006.01) |
| *A61F 13/15* | (2006.01) |

(52) U.S. Cl.
CPC ................ *A61K 33/00* (2013.01); *A61F 5/30* (2013.01); *A61F 13/00063* (2013.01); *A61F 13/141* (2013.01); *A61F 13/8405* (2013.01); *A61M 35/10* (2019.05); *C01B 3/061* (2013.01); *C01B 13/0207* (2013.01); *A61F 2013/16* (2013.01); *A61M 2202/02* (2013.01)

(58) Field of Classification Search
None
See application file for complete search history.

(56) References Cited

U.S. PATENT DOCUMENTS

| | | | |
|---|---|---|---|
| 6,890,553 B1 * | 5/2005 | Sun ........................ | A61F 7/034 424/400 |
| 8,790,384 B2 * | 7/2014 | Uchiyama ................ | A61F 7/03 607/112 |

* cited by examiner

*Primary Examiner* — Susan T Tran
(74) *Attorney, Agent, or Firm* — WPAT, PC

(57) ABSTRACT

A hydrogen-supplying breathable layer in the present disclosure comprises: a thin layer wrapping a hydrogen-producing formula inside, having an airtight outer side as well as an air-permeable inner side on which a plurality of micro pores are opened and featuring a monolayer or a composite layer; a hydrogen-producing formula wrapped inside the thin layer and not dissipated but absorbing moistures in air or liquid water for generation of hydrogen; hydrogen permeating a plurality of micro pores and released to skin and intra-corporal parts. The hydrogen-producing formula in the hydrogen-supplying breathable layer comprises metal peroxides (metal hydroxides or metal hydrides) and aluminum powders (or silica powders); the breathable layer is applicable to a dressing pack or other sanitary paraphernalia in daily lives for relieving non-bacteria inflammations and promoting health care effects.

12 Claims, 7 Drawing Sheets

MICROENVIRONMENT HYDROGEN-SUPPLYING BREATHABLE LAYER AND APPLICATIONS THEREOF

BACKGROUND OF THE INVENTION

1. Field of the Invention

A breathable layer with a hydrogen-producing formula provided in the present disclosure for life health is able to supply nonirritating and well-diffusible hydrogen but no harmful by-products during reactions, to skin or intra-corporal body parts for health care and disease relief.

2. Description of the Prior Art

Hydrogen ($H_2$), a colorless and odorless gas which is an antioxidant in cancer therapy according to the research published in 1975, was used to neutralize toxic free radicals for treatment of cerebral ischemia-reperfusion injury by Japanese researchers in 2007 and further demonstrated therapeutic effects on several diseases or injuries in many research reports. Hydrogen, which is known for anti-oxidative, anti-inflammatory and anti-apoptosis effects after neutralizing free radicals optionally, has no adverse effect on reactive oxygen for intra-corporal physiological actions such as superoxide anion and hydrogen peroxide and is applicable to the human body safely. Additionally, hydrogen critically acclaimed for its strong diffusivity and not obstructed by cell membranes or various biological barriers reaches out to any body part, serving as a curative gas for acute and chronic diseases including stroke, diabetes, arteriosclerosis and Parkinson's disease.

Hydrogen can be absorbed through respiration, potable hydrogen water or hypodermic hydrogen-rich saline. Hydrogen absorbed in the human body relieves symptoms of nerve or cardiovascular diseases including stroke and myocardial infarction; hydrogen water in the human body has curative effects on diabetes or metabolic diseases reportedly or relieves allergic diseases such as atopic dermatitis in the animal model; hydrogen has been injected into an eyeball with retinopathy directly for treatment of fundus oculi diseases. In a program launched by Kagoshima University, Japan, and Sam Ratulangi University, Indonesian, hydrogen was demonstrated promotion of tumor cell apoptosis, the obvious effect of fluorouracil (5-FU) as an antineoplastic and the lifespan of an animal with a tumor in cytological and animal models in which high-concentration hydrogen water and fluorouracil were administrated.

In normal applications, hydrogen is supplied from hydrogen water or a high-pressure hydrogen vessel. In this regard, a bulky power-hungry machine for manufacturing of hydrogen is prepared for dissolving hydrogen in water but produced hydrogen water is difficultly preserved; high-purity hydrogen is usually stored in a high-pressure steel cylinder which is bulky, heavy and inconvenient for carrying and jeopardizes safety for a user. Accordingly, the application of hydrogen is difficultly promoted and restrictive because a machine for manufacturing of hydrogen or a high-pressure steel cylinder is not a user-friendly appliance. Against this background, how to supply hydrogen available at all times and places for non-bacterial inflammations or other health care effects is an issue to be overcome in the present disclosure.

The diversified sanitary products in daily lives available in the market, for example, gauze mask, face shield and facial mask, all of which should contact with skin directly, are widely advertised as comfortable and convenient paraphernalia. On the other hand, other is products which supply good gases such as oxygen to the human body through reactions of internal materials have been invented by persons skilled in the art and committed to promoting and creating new applications for synergic effects. However, the gases are generated from chemical reactions between materials, which probably consist of many materials or a combination of multiple materials simultaneously for health care effects, and spawn risks including material dissipation or unsafe by-products.

Accordingly, a breathable layer for supply of hydrogen to a sanitary product in daily lives is an important issue to be settled in the present disclosure.

SUMMARY OF THE INVENTION

To settle the above problems, a hydrogen-supplying breathable layer disclosed by the applicant comprises: a thin layer wrapping a hydrogen-producing formula inside, having an airtight outer side as well as an air-permeable inner side on which a plurality of micro pores are opened and featuring a monolayer or a composite layer; a hydrogen-producing formula wrapped inside the thin layer and not dissipated but absorbing moistures in air or liquid water for generation of hydrogen; hydrogen permeating a plurality of micro pores and released to skin and intra-corporal parts.

To this end, the inner side of the thin layer can be made of silica gel, nonwovens or plastic breathable film.

To this end, the outer side of the thin layer can be made of polypropylene or polyethylene membrane, aluminum coating or composite membrane.

To this end, the hydrogen-producing formula can be powdered or granulated.

To this end, the hydrogen-producing formula comprises metal peroxides (metal hydroxides or metal hydrides) and aluminum powders (or silica powders).

To this end, the weight ratios of metal peroxides or metal hydroxides to aluminum powders range from 1:100 to 100:1, preferably from 1:10 to 10:1.

To this end, the metal peroxides are selected from a group of metal peroxides consisting of calcium peroxide, magnesium peroxide, sodium peroxide and potassium peroxide; the metal hydroxides are selected from a group of metal hydroxides consisting of calcium hydroxide, magnesium hydroxide, sodium hydroxide and potassium hydroxide; the metal hydrides are selected from a group of metal hydrides consisting of magnesium hydride, calcium hydride and silicon hydride.

To this end, the hydrogen-producing formula may comprise solid acids which are selected from a group of solid acids consisting of solid citric acid, solid lactic acid, solid oxalic acid, solid hydrochloric acid, solid phytic acid and solid silicic acid.

To this end, the hydrogen-producing formula further comprises super absorbent polymers, activators or catalysts.

To this end, the thin layer further comprises a unit for production of oxygen and active oxygen.

To this end, the breathable layer is applicable to sanitary paraphernalia in daily lives which comprises eye patch, gauze mask, face shield, facial mask, bra, breast pasty, breast pad, sanitary towel (napkin), paper diaper, panty liner, wound dressings, band aid, gauze, anti-bedsore pad and dressing pack.

A dressing pack provided in the present disclosure comprises:

a thin layer wrapping a hydrogen-producing formula and an oxygen-producing formula inside, having an airtight outer side as well as an air-permeable inner side on which a plurality of micro pores are opened and featuring a monolayer or a composite layer;

a hydrogen-producing formula wrapped inside the thin layer and not dissipated but absorbing moistures in air or liquid water for generation of hydrogen;

hydrogen permeating a plurality of micro pores and released to skin;

an oxygen-producing formula wrapped inside the thin layer and not dissipated but absorbing moistures in air or liquid water for generation of oxygen;

oxygen permeating a plurality of micro pores and released to skin.

To this end, the inner side of the thin layer can be made of silica gel, nonwovens or plastic breathable film.

To this end, the outer side of the thin layer can be made of polypropylene or polyethylene membrane, aluminum coating or composite membrane.

To this end, the hydrogen-producing formula or the oxygen-producing formula can be powdered or granulated.

To this end, the hydrogen-producing formula comprises metal peroxides (metal hydroxides or metal hydrides) and aluminum powders (or silica powders).

To this end, the weight ratios of metal peroxides or metal hydroxides to aluminum powders range from 1:100 to 100:1, preferably from 1:10 to 10:1.

To this end, the metal peroxides are selected from a group of metal peroxides consisting of calcium peroxide, magnesium peroxide, sodium peroxide and potassium peroxide.

To this end, the metal hydroxides are selected from a group of metal hydroxides consisting of calcium hydroxide, magnesium hydroxide, sodium hydroxide and potassium hydroxide.

To this end, the metal hydrides are selected from a group of metal hydrides consisting of magnesium hydride, calcium hydride and silicon hydride.

To this end, the hydrogen-producing formula may comprise solid acids which are selected from a group of solid acids consisting of solid citric acid, solid lactic acid, solid oxalic acid, solid hydrochloric acid, solid phytic acid and solid silicic acid for the pH value between 4 and 9.

To this end, the oxygen-producing formula comprises metal peroxides which are selected from a group of metal peroxides consisting of calcium peroxide, magnesium peroxide, sodium peroxide and potassium peroxide.

To this end, the weight ratios of the oxygen-producing formula to the hydrogen-producing formula range from 1:1 to 1:50.

To this end, the inflammation means the non-bacteria inflammation.

In the present disclosure, a breathable layer with a hydrogen-producing formula inside produces much hydrogen quickly, supplies hydrogen to skin, nostrils, mouth, eyes or other body parts to be contacted, and shows advantages as follows:

(1) Safe and convenient application:
A breathable layer which is not connected with a tube from a steel vessel or electrically connected is classified as portable, harmless and user-friendly paraphernalia.

(2) No harmful by-products derived.

(3) Paraphernalia adhered to and easily absorbed by skin.

(4) Hydrogen produced for health care applications widely:
Good diffusivity for reaching out to body parts without limitation.
Nontoxic, mild and safe reducing agent.
Neutralization of free radicals and good anti-oxidation and anti-inflammation, particularly non-bacteria inflammation, effects.
Enriching of intra-corporal microbe flora.

(5) Addition of oxygen to dressings for no oxygen deficit which is common in traditional dressings applied on skin too long.

The present disclosure also discloses preferred weight ratios of a hydrogen-producing formula to an oxygen-producing formula and dosages of the formulae for better health care effects as shown in embodiments in which a breathable layer is applicable to sanitary paraphernalia in daily lives and further applications.

DETAILED DESCRIPTION OF THE PREFERRED EMBODIMENT

A hydrogen-supplying breathable layer explained in the following embodiments for specific features, applications and advantages of a breathable layer should not be limited to the embodiments. Any equivalent application or modification without departing from the spirit of the present disclosure should be incorporated in claims hereinafter.

Figure 1:
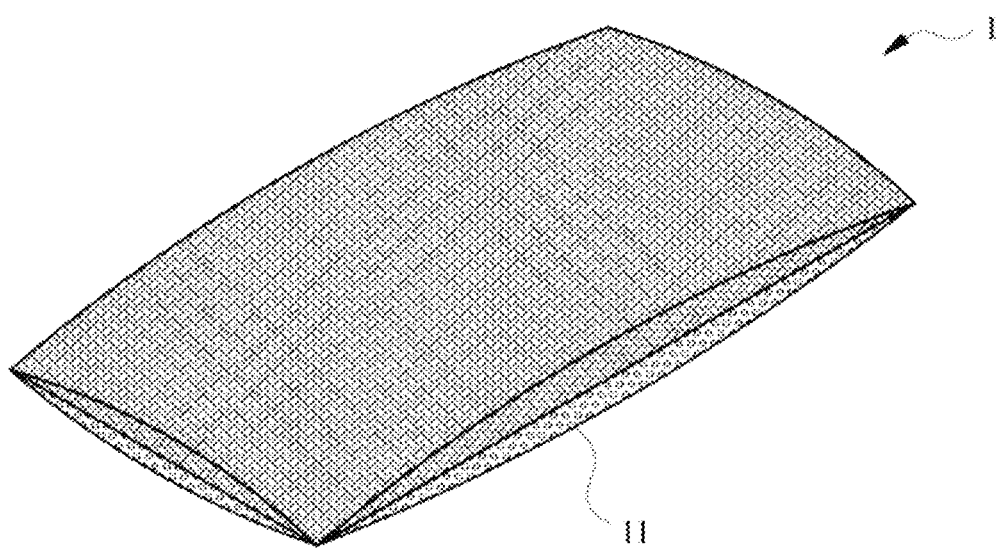
FIG. 1 is a schematic view of a hydrogen-supplying breathable layer.
Figure 2:
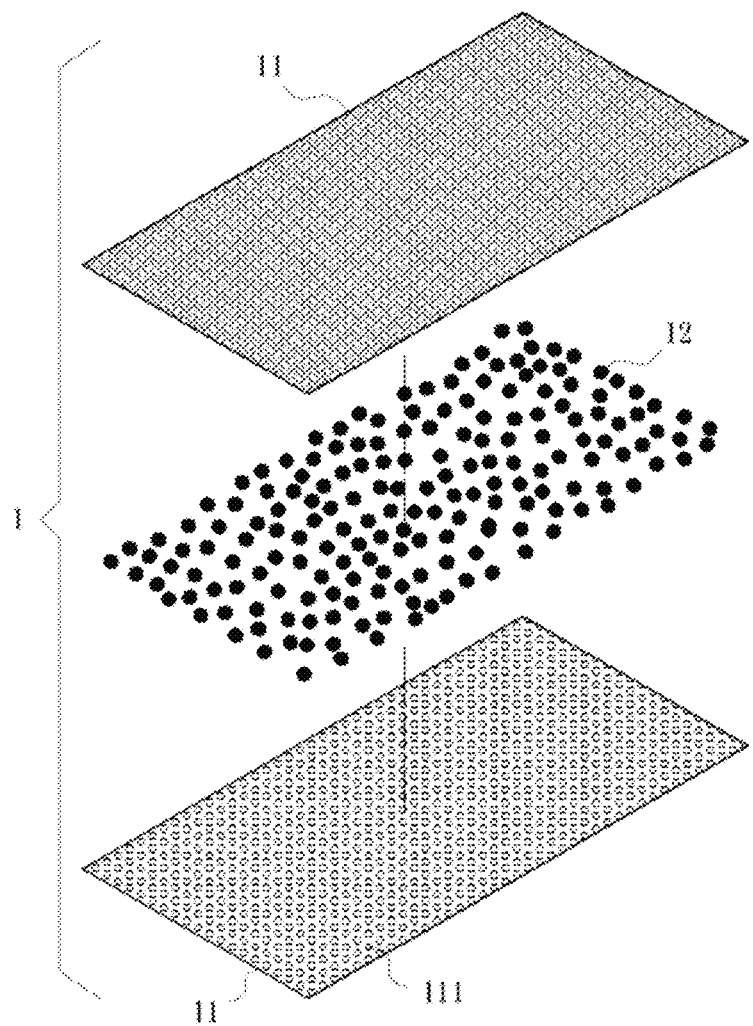
FIG. 2 is an exploded view of a breathable layer.
Figure 3:
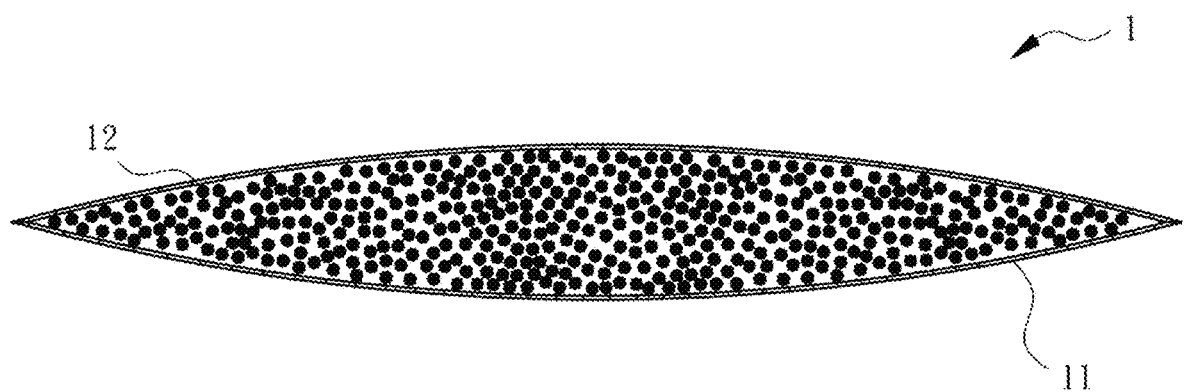
FIG. 3 is a cross-sectional view of a breathable layer.

As shown in FIG. 1 to FIG. 3, a breathable layer 1 provided in the present disclosure comprises: a thin layer 11 wrapping a hydrogen-producing formula inside, having an airtight outer side as well as an air-permeable inner side on which a plurality of micro pores 111 are opened and featuring a monolayer or a composite layer; a hydrogen-producing formula 12 wrapped inside the thin layer 11 and not dissipated but absorbing moistures in air or liquid water for generation of hydrogen. As shown in FIG. 2, hydrogen permeating a plurality of micro pores 111 is absorbed by the human body through skin, nostrils, a mouth, eyes or other contact positions.

In the present disclosure, the hydrogen-producing formula 12 is wrapped by the thin layer 11 having an airtight outer side and an air-permeable inner side on which micro pores 111 are opened wherein the micro pores 111 have bore diameters less than diameters of ingredients in the hydrogen-producing formula 12 for no exposure of the hydrogen-producing formula 12 and the outer side and the inner side of the thin layer 11 is made of an airtight material and a skin-friendly material, respectively.

The hydrogen-producing formula 12 is packed in an airtight material for no reactions between the hydrogen-producing formula 12 and moistures in air early; the hydrogen-producing formula 12 from which an airtight packaging can be removed is applicable to a body part as required. In practice, the breathable layer 1 proves effective in preserving perspiration or moistures inside the airtight outer side such that the hydrogen-producing formula 12 reacts adequately for directive supply of hydrogen to skin.

The inner side of the thin layer 11 wrapping the hydrogen-producing formula 12 can be made of silica gel, nonwovens or plastic breathable film; the outer side of the thin layer 11 can be made of polypropylene or polyethylene membrane, aluminum coating or composite membrane.

The hydrogen-producing formula 12 which is either powdered or granulated comprises metal peroxides (metal hydroxides or metal hydrides) and aluminum powders (or silica powders).

Furthermore, the metal peroxides are selected from a group of metal peroxides consisting of calcium peroxide, magnesium peroxide, sodium peroxide and potassium peroxide; the metal hydroxides are selected from a group of metal hydroxides consisting of calcium hydroxide, magnesium hydroxide, sodium hydroxide and potassium hydroxide.

The hydrogen-producing formula 12 also comprises compounds which react with water for production of metal hydroxides such as magnesium hydride, calcium hydride and silicon hydride.

In the hydrogen-producing formula 12, solid acids used to neutralize the hydrogen-producing formula 12 are optionally added for the pH value between 4 and 9 during which skin is not irritated and hydrogen is absorbed increasingly; the solid acids are selected from a group of acids consisting of solid citric acid, solid lactic acid, solid oxalic acid, solid hydrochloric acid, solid phytic acid and solid silicic acid.

The mechanism for supply of hydrogen from the hydrogen-producing formula is shown as follows:

Metal peroxides react with water first to produce metal hydroxides and release oxygen, as shown in the following reaction formulae.

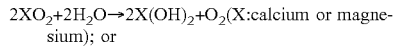

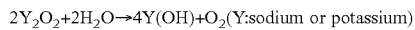

Metal hydroxides react with aluminum powders to produce hydrogen, as shown in the following reaction formulae.

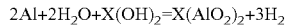

Metal hydrides react with water to produce hydrogen and metal hydroxides which further react with water for production of hydrogen continuously.

In the above chemical reactions, highly active alkali metal (Group IA elements, e.g., sodium or potassium) peroxides or hydroxides could be selected as reactants for production of much hydrogen quickly.

As shown in previous embodiments for various reactions based on the hydrogen-producing formula, other reactions between silicon and water/metal hydroxides for production of hydrogen well known to persons skilled in the art should be taken as equivalent applications and incorporated in claims for the hydrogen-producing formula in the present disclosure. The reactions are shown as follows:

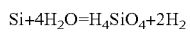

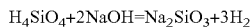

Furthermore, a powdered or granulate oxygen-producing formula 13 which comprises metal peroxides or metal superoxides inside could be added in the thin layer 11 for prevention of skin contacting with dressings too long from irritation due to oxygen deficit at an airtight outer side of the thin layer 11.

Metal peroxides react with water for release of oxygen, as shown in following reaction formulae:

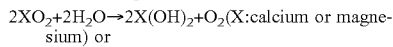

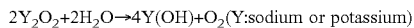

For better proportions between reactants, the efficiencies of hydrogen produced with reactants (weights from 0.01 to 100 grams) are tested. In the hydrogen-producing formula, the weight ratios of metal peroxides or metal hydroxides to aluminum powders are defined as 1:100 to 100:1 for production of hydrogen generally or 1:10 to 10:1 preferably. For production of oxygen released out of the thin layer 1, the weight ratios of the oxygen-producing formula to the hydrogen-producing formula could be defined as 1:1 to 1:50.

Figure 4:
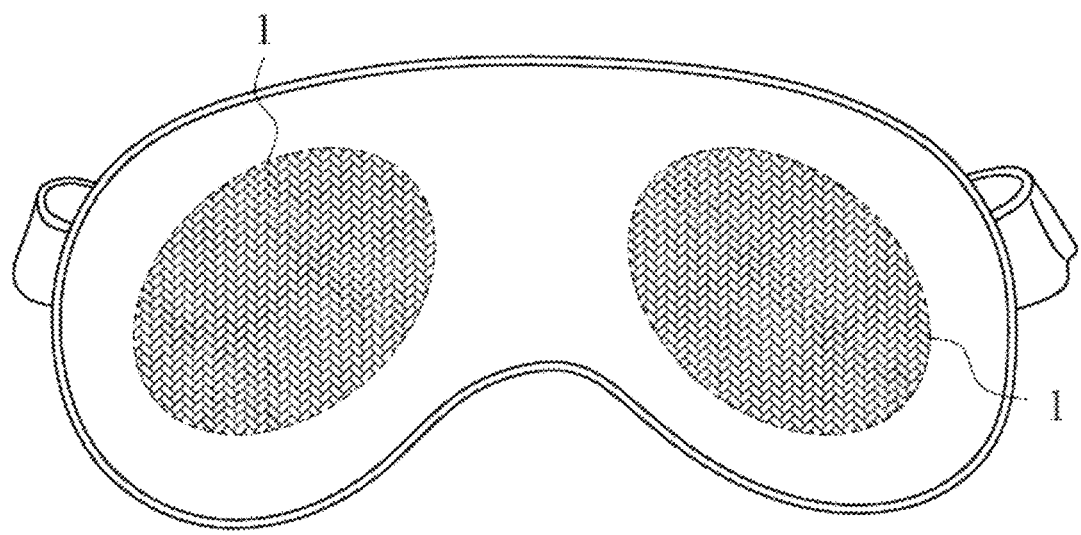
FIG. 4 is a schematic view of a breathable layer applicable to an eye patch.
Figure 5A:
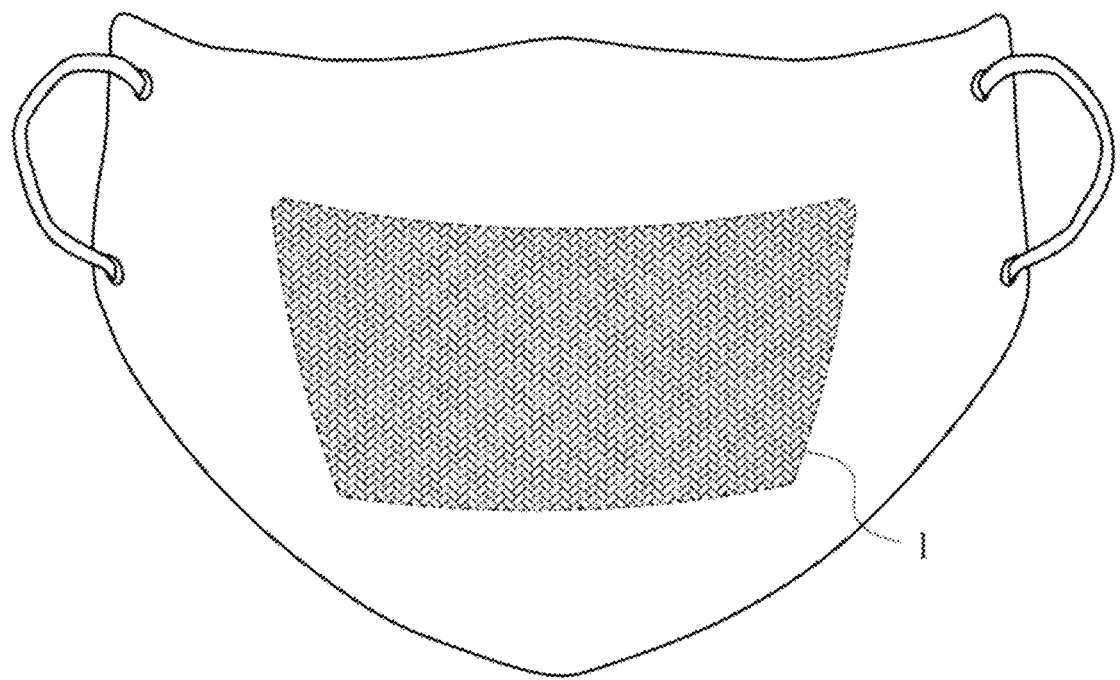
FIGS. 5A and 5B are schematic views of a breathable layer applicable to gauze masks.
Figure 5B:
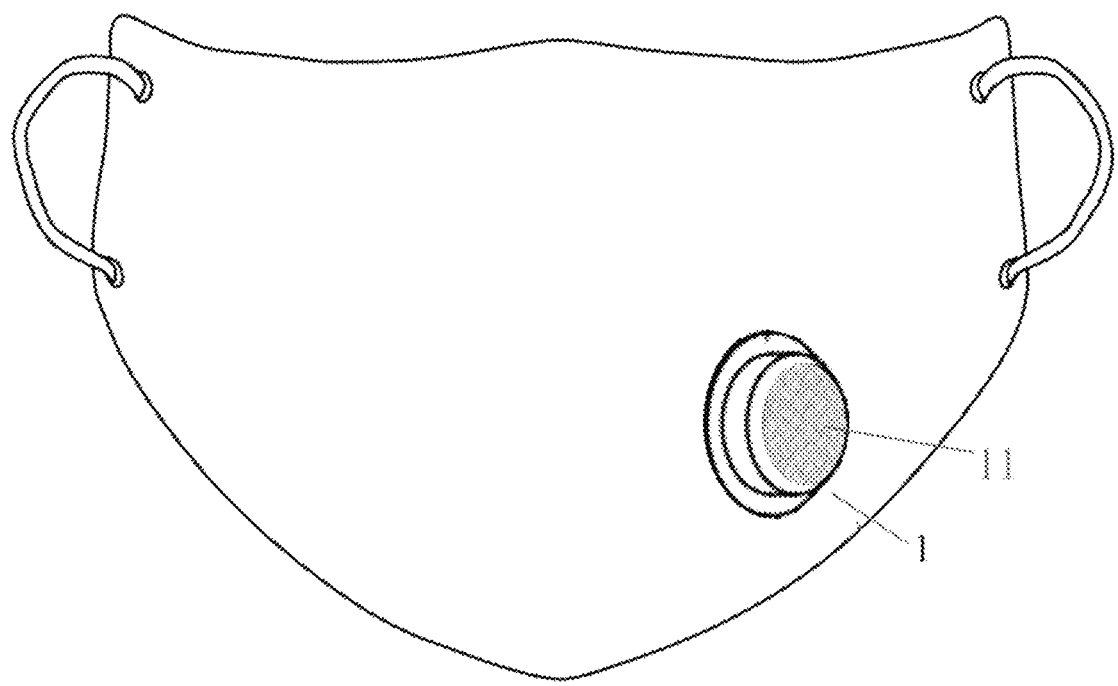
Figure 6:
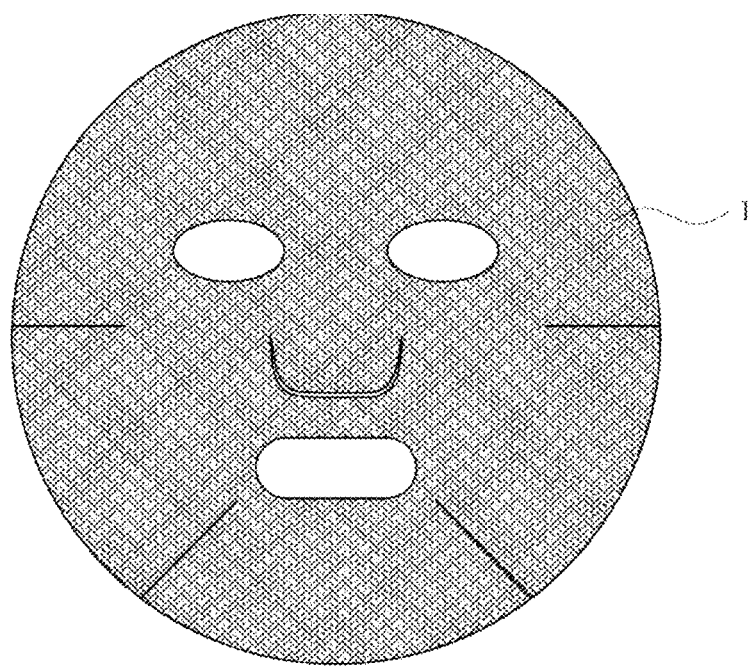
FIG. 6 is a schematic view of a breathable layer applicable to a facial mask.
Figure 7:
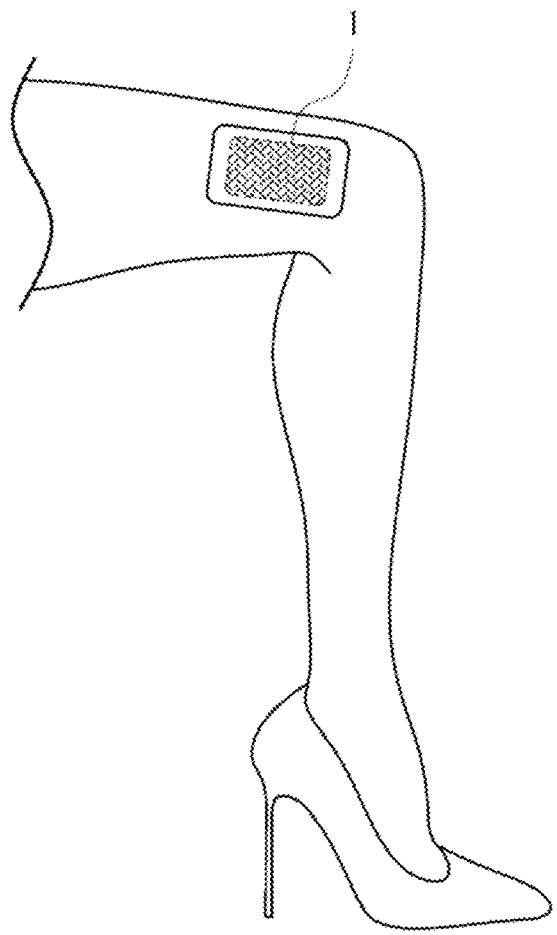
FIG. 7 is a schematic view of a breathable layer applicable to wound dressings.

A breathable layer is applicable to sanitary paraphernalia in daily lives which include, without limitation, eye patch (FIG. 4), gauze mask (FIGS. 5A, 5B), face shield, facial mask (FIG. 6), bra, breast pasty, breast pad, sanitary towel (napkin), paper diaper, panty liner, wound dressings (FIG. 7), band aid, gauze, anti-bedsore pad and dressing pack.

In the present disclosure, sanitary paraphernalia with breathable layers inside such as gauze masks, eye patches, facial masks or wound dressings were distributed to recruited subjects, who suffered from nerve disease, constipation, UV-induced damage, eyestrain, eye discomfort or trauma or received the radioactive therapy, and used for three months (three times a week; two hours every time). In is questionnaires submitted by subjects having finished tests, the states including symptom relief and comfort for the hydrogen-producing formula of the breathable layer used in sanitary paraphernalia were evaluated by ratings from 1 (weakest effect) to 10 (most significant effect). Moreover, the breathable layer in the present disclosure was compared with other ordinary products from which no gas was produced (referred to as commercial products hereinafter) or products in which no aluminum powder was added (and no hydrogen was produced). The ratings based on means are shown as follows. The hydrogen-producing formula in a breathable layer refers to preferred weight ratios mentioned previously (metal peroxides or metal hydroxides: aluminum powders=100:80~120) which were adjusted according to corresponding sanitary paraphernalia.

Embodiment 1

Gauze Mask

The test groups and results are shown in Table 1. Reactants include 10 g calcium peroxides (metal peroxides), 10 g calcium hydroxides (metal hydroxides), 1 g aluminum powders and adequate citric acids for reactions with skin moistures or added water and production of hydrogen.

As shown in test results, the hydrogen-producing formula in the present disclosure proves effective in symptom reliefs of nerve disease, side effect from radioactive therapy and constipation that are not observed in a commercial mask or another formula for production of oxygen only in which no aluminum powders are added. Moreover, a subject's comfort for the application of a hydrogen-producing formula in which reactants are changed is better than a commercial gauze mask or further promoted with peroxides, hydroxides and solid acids added simultaneously.

TABLE 1 symptom reliefs of different diseases and comfort attributed to the breathable layer in a gauze mask

| Symptom relief/comfort | Formula without $H_2$/$O_2$ produced Commercial product | Hydrogen-producing formula ($H_2$ (majority) and $O_2$ (minority) produced) | | | Only $O_2$ produced |
|---|---|---|---|---|---|
| | | Metal peroxides + aluminum powders | Metal hydroxides + aluminum powders | Metal peroxides + metal hydroxides + solid acids | Metal peroxides without aluminum powders added |
| Nerve disease | 1 | 5 | 6 | 8 | 2 |
| Side effect from radioactive therapy | 0 | 5 | 5 | 6 | 3 |
| Constipation | 1 | 6 | 7 | 8 | 2 |
| Comfort | 3 | 5 | 5 | 6 | 5 |

Embodiment 2

Eye Patch

The test groups and results are shown in Table 2. Reactants include 1-10 g sodium peroxides (metal peroxides), 1-10 g sodium hydroxides (metal hydroxides), 10 g aluminum powders and adequate oxalic acids for reactions with added water and production of hydrogen.

As shown in test results, the hydrogen-producing formula in the present disclosure proves effective in good symptom reliefs of eyestrain, eye disease and floaters in contrast to a commercial eye patch or another formula with which no hydrogen is produced because of no aluminum powder added. Moreover, a subject's comfort for the application of a hydrogen-producing formula in which reactants are changed is better than a commercial eye patch; particularly, a subject's comfort for the application of a hydrogen-producing formula in which peroxides, hydroxides and solid acids are added or both a hydrogen-producing formula and an oxygen-producing formula for production of much hydrogen and oxygen are mixed is further promoted. For that matter, an oxygen-producing formula contributes to relief of skin discomfort induced by oxygen deficit of skin which contacts with a dressing pack too long.

TABLE 2 symptom reliefs of different diseases and comfort attributed to the breathable layer in an eye patch

| Symptom relief/comfort | Formula without $H_2$/$O_2$ produced Commercial product | Hydrogen-producing formula | | | | Only $O_2$ produced |
|---|---|---|---|---|---|---|
| | | $H_2$ (majority) $O_2$ (minority) | | | $H_2$ (majority) $O_2$ (majority) | |
| | | Metal peroxides + aluminum powders | Metal hydroxides + aluminum powders | Metal peroxides + metal hydroxides + solid acids | Metal peroxides + aluminum powders + solid acids | Metal peroxides without aluminum powders added |
| Eyestrain | 3 | 7 | 8 | 9 | 9 | 4 |
| Eye disease | 1 | 6 | 7 | 8 | 8 | 2 |
| Floaters | 0 | 7 | 6 | 7 | 8 | 2 |
| Comfort | 3 | 6 | 6 | 7 | 10 | 6 |

Embodiment 3

Facial Mask

The test groups and results are shown in Table 3. Reactants include 12.5 g magnesium peroxides (metal peroxides), 12.5 g magnesium hydroxides (metal hydroxides), 6.25 g silica powders and adequate lactic acids (solid acids) for reactions with added water and production of hydrogen.

As shown in test results, the hydrogen-producing formula in the present disclosure proves effective in good symptom reliefs of ultraviolet injury, side effect from radioactive therapy and nerve disease in contrast to a commercial facial mask or another formula with which no hydrogen is produced due to no aluminum powder added. Moreover, a subject's comfort for the application of a hydrogen-producing formula in which reactants are changed is better than a commercial facial mask; particularly, a subject's comfort for the application of a hydrogen-producing formula in which peroxides, hydroxides and solid acids are mixed is further promoted.

TABLE 3 symptom reliefs of different diseases and comfort attributed to the breathable layer in a facial mask

| Symptom relief/comfort | Formula without $H_2/O_2$ produced Commercial product | Hydrogen-producing formula ($H_2$ (majority) and $O_2$ (minority) produced) | | | Only $O_2$ produced Metal peroxides without silica powders added |
|---|---|---|---|---|---|
| | | Metal peroxide + aluminum powders | Metal hydroxide + silica powders | Metal peroxides + metal hydroxides + solid acids | |
| Ultraviolet injury | 1 | 5 | 6 | 8 | 1 |
| Side effect from radioactive therapy | 1 | 5 | 7 | 9 | 2 |
| Nerve disease | 2 | 6 | 7 | 8 | 2 |
| Comfort | 3 | 7 | 6 | 8 | 7 |

Embodiment 4

Wound Dressings

The test groups and results are shown in Table 4. Reactants include 2.5 g potassium peroxides (metal peroxides), 2.5 g potassium hydroxides (metal hydroxides), 2.5 g aluminum powders and adequate phytic acids (solid acids). Hydrogen is produced from wound dressings in which water has been absorbed and retained but not released to a wound reversely. Moreover, hydrogen is supplied from the breathable layer which is ventilated in design for no double infection at the wound.

As shown in test results, the hydrogen-producing formula in the present disclosure proves effective in symptom reliefs of ultraviolet injury, side effect from radioactive therapy and trauma in contrast to commercial wound dressings or another formula with which no hydrogen is produced due to no aluminum powder added. Moreover, a subject's comfort for the application of a hydrogen-producing formula in which reactants are changed is better than commercial wound dressings; particularly, a subject's comfort for the application of a is hydrogen-producing formula in which peroxides, hydroxides and solid acids are mixed is further promoted.

TABLE 4 symptom reliefs of different diseases and comfort attributed to the breathable layer in wound dressings

| Symptom relief/comfort | Formula without $H_2/O_2$ produced Commercial product | Hydrogen-producing formula $H_2$ (majority) and $O_2$ (minority) produced | | | Only $O_2$ produced Metal peroxide without aluminum powders added |
|---|---|---|---|---|---|
| | | Metal peroxides + aluminum powders | Metal hydroxides + aluminum powders | Metal peroxides + metal hydroxides + solid acids | |
| Ultraviolet injury | 1 | 6 | 5 | 8 | 2 |
| Side effect from radioactive therapy | 1 | 6 | 4 | 7 | 2 |

TABLE 4-continued symptom reliefs of different diseases and comfort attributed to the breathable layer in wound dressings

| Symptom relief/comfort | Formula without $H_2/O_2$ produced Commercial product | Hydrogen-producing formula $H_2$ (majority) and $O_2$ (minority) produced | | | Only $O_2$ produced |
|---|---|---|---|---|---|
| | | Metal peroxides + aluminum powders | Metal hydroxides + aluminum powders | Metal peroxides + metal hydroxides + solid acids | Metal peroxide without aluminum powders added |
| Wound healing | 0 | 5 | 4 | 7 | 2 |
| Comfort | 2 | 5 | 4 | 6 | 4 |

Embodiment 5

Dressing Pack

In the present disclosure, a dressing pack in which peroxides as oxygen-producing materials are added for generation of much oxygen prevents skin contacting with a dressing pack too long from oxygen deficit or skin discomfort. Absorbing moistures for production of hydrogen/oxygen and moderating reverse moisture leakage to a wound, wound dressings inside the breathable layer which promotes ventilation of gases only and supply of hydrogen in design eases skin discomfort attributed to oxygen deficit at a wound.

Embodiment 5-1

Gout

Figure 8A:
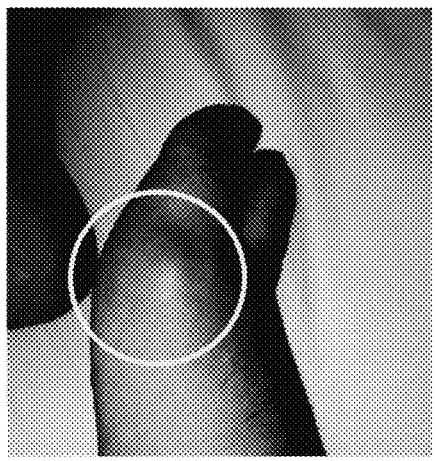
FIG. 8A illustrates a body part affected by gout without application of a dressing pack.
Figure 8B:
FIG. 8B illustrates the effect of a dressing pack which was stuck on a body part affected by gout two hours later.
Figure 8C:
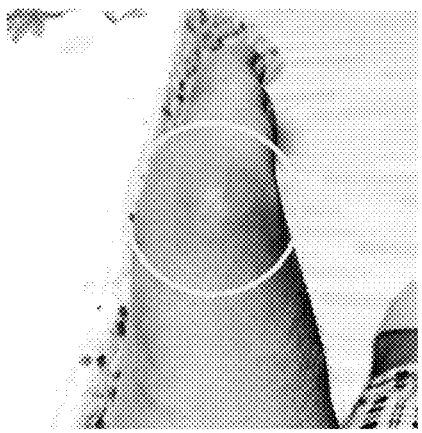
FIG. 8C illustrates the effect of a dressing pack which was stuck on a body part affected by gout three hours later.
Figure 8D:
FIG. 8D illustrates the effect of a dressing pack which was stuck on a body part affected by gout at Day 4.

As shown in FIG. 8, the big toe on the right foot of a 55-year-old male subject suffering from a gout attack was red, swollen and serious painful (FIG. 8A). When a dressing pack on which moistures were sprayed was adhered to the red and swollen big toe, the pain of the subject was alleviated obviously after one hour. After a new dressing pack was stuck by the subject every one hour, for example, the second dressing pack in FIG. 8B and the third dressing pack in FIG. 8C, the swelling due to gout subsided by 40%. Finally, the swelling disappeared (FIG. 8D) and no skin allergy/discomfort attributed to a dressing pack contacting with skin was felt when the tenth dressing pack at Day 4 was applied by the subject following the rule of administrating three dressing packs every day. In the present disclosure, a dressing pack comprises 2.5 g calcium peroxides and 1.5 g aluminum powders for production of much hydrogen and oxygen.

Embodiment 5-2

Ankle Strain

Figure 9:
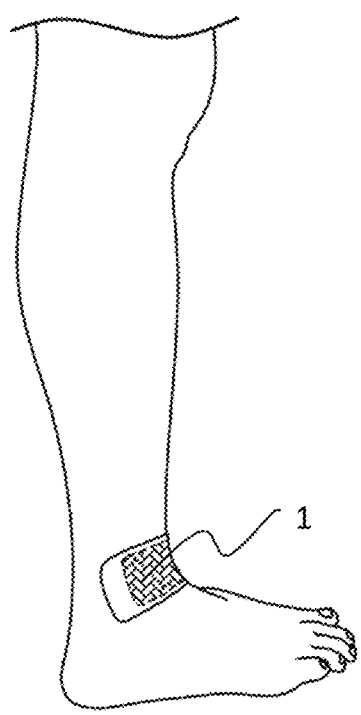
FIG. 9 is a schematic view of a dressing pack stuck on a sprained ankle.

A dressing pack on which moistures were sprayed was administered to a 65-year-old male subject, who had sprained his ankle and walked with difficulty, at Day 4 (FIG. 9). The pain felt by the subject dropped by 50% after 10 minutes and 70% after 20 minutes dramatically. Finally, the subject, who felt no pain or skin allergy/discomfort due to the dressing pack contacting with skin, walked normally one hour later.

Embodiment 5-3

Pain in the Cervical Spine

After a dressing pack on which moistures were sprayed was administered to a 60-year-old male subject who had suffered from pain in the cervical spine for over 20 years, the subject felt less pain dramatically and no skin allergy/discomfort due to the dressing pack contacting with skin 30 minutes later.

Embodiment 5-4

Premenstrual Distension of Breast

A 21-year-old female subject having suffered from the premenstrual syndrome, for example, premenstrual distension of breast was recruited. The female subject, who felt premenstrual distension of breast, stuck dressing packs on which moistures were sprayed on breasts and felt less pain dramatically and no skin allergy/discomfort due to the dressing pack contacting with skin one hour later. In the present disclosure, the dressing pack comprises 2.5 g calcium peroxides and 1.5 g aluminum powders for production of much hydrogen and oxygen.

Embodiment 5-5

Menstrual Pain

Figure 10:
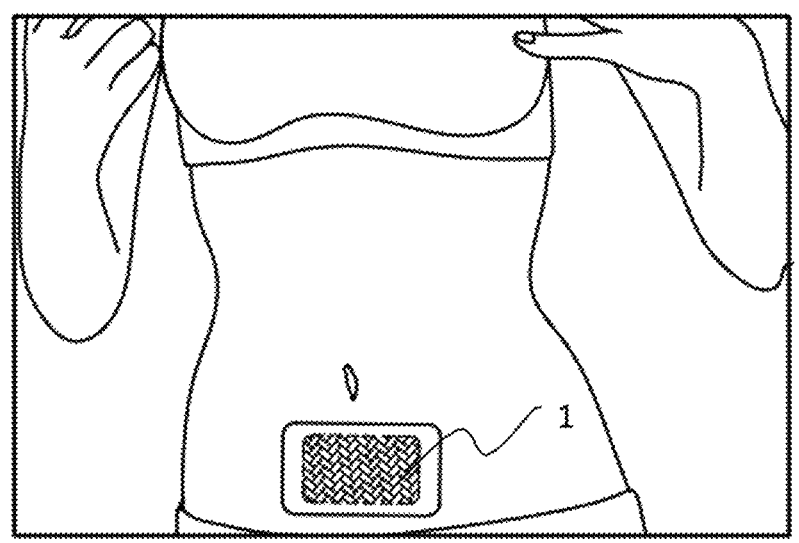
FIG. 10 is a schematic view of a dressing pack stuck on a patient who was annoyed at menstrual pain.

A 30-year-old female subject with endometriosis was annoyed at menstrual pain during her menstrual period. The subject who was suffering from menstrual pain stuck a dressing pack on which moistures were sprayed next to her belly bottom (FIG. 10) and felt less pain dramatically 10 minutes later. In the following three days, she applied dressing packs eight hours every day and felt no skin allergy/discomfort attributed to dressing packs contacting with skin. In the present disclosure, a dressing pack comprises 1 g magnesium peroxides, 1.5 g potassium hydroxides, 1.5 g aluminum powders and adequate phytic acids for production of much hydrogen and oxygen.

Embodiment 5-6

Hip Pain

A 55-year-old male subject who was upset about hip pain chronically stuck a dressing pack on which moistures were sprayed at the pain and felt much better 20 minutes later and no skin allergy/discomfort attributed to a dressing pack contacting with skin. As shown in test results, a combination of a hydrogen-producing formula and an oxygen-producing formula in the present disclosure proves effective in moderating inflammation or pain at muscles, bones or viscera but avoiding skin allergy/discomfort attributed to skin contacting with a dressing pack in contrast to other commercial dressing packs.

In a sanitary towel (napkin) for no fluid leakage particularly, a hydrogen-supplying breathable layer in which polymer absorbent materials (super absorbent polymers) are added absorbs liquids and produces hydrogen to avoid skin inflection/inflammation due to liquid backflows.

In summary, a breathable layer in which a distinct hydrogen-producing formula is incorporated for sanitary paraphernalia in daily lives relieves symptoms of nerve disease, side effect from radioactive therapy, constipation, ultraviolet injury, eyestrain, eye discomfort or trauma, breaking the mold of traditional sanitary products by anti-oxidative hydrogen enriching intra-corporal microbe flora. Compared with another formula (without aluminum powders) for production of hydrogen only, a hydrogen-producing formula in the present disclosure embodies better and diversified health care effects in applications. Furthermore, a breathable layer with an oxygen-producing formula added provides a user with better comfort and ventilation than a commercial product (a formula without oxygen produced). Preferably, a breathable layer in which peroxides, hydroxides and solid acids are added is effective in relieving some symptoms and promoting comfort.

Moreover, much hydrogen and/or oxygen produced by a is breathable layer in the present disclosure quickly is supplied to skin, nostrils, mouth, eyes or other body parts to be contacted directly rather than through a tube connected with a steel cylinder or a power-driven gas generator common in a traditional hydrogen generation method or appliance; a breathable layer with a portable, harmless and environment-friendly formula closely adhered to skin produces hydrogen easily without residues of hazardous by-products.

Additionally, as a nontoxic, mild and safe reducing agent, hydrogen known for its simple structure performs well in diffusivity, reaching out to any body part without restriction, neutralizing free radicals and enriching intra-corporal microbe flora. Compared with a traditional sanitary product, hydrogen promotes health care widely and effectively.

In addition to diseases mentioned in embodiments of the present disclosure, other disease such as cancer, side effect of chemotherapy, metabolic disease, immunological disease, allergy, diabetes, obesity, colitis and non-bacterial inflammation can be rationally relieved by a breathable layer from which hydrogen to neutralize free radicals is generated.

For production of much hydrogen, a hydrogen-producing formula may further comprise super absorbent polymers, activators or catalysts as appropriate. Moreover, a unit for production of oxygen and active oxygen may be incorporated in a hydrogen-producing formula pro rata for different requirements and effects.

The above detailed descriptions are feasible embodiments of a hydrogen-supplying breathable layer that should not restrict claims of the present disclosure. Any equivalent application or modification without departing from the spirit of the present disclosure should be incorporated in claims hereinafter.

In summary, a hydrogen-supplying breathable layer in the present application meets novelty and non-obviousness for patentability.

What is claimed is:

1. A dressing pack for anti-inflammation, comprising:
a thin layer wrapping a hydrogen-producing formula and an oxygen-producing formula inside, having an airtight outer side as well as an air-permeable inner side on which a plurality of micro pores are opened and featuring a monolayer or a composite layer;
a hydrogen-producing formula wrapped inside the thin layer and not dissipated but absorbing moistures in air or liquid water for generation of hydrogen;
hydrogen permeating a plurality of micro pores and released to skin;
an oxygen-producing formula wrapped inside the thin layer and not dissipated but absorbing moistures in air or liquid water for generation of oxygen;
oxygen permeating a plurality of micro pores and released to skin;
wherein the hydrogen-producing formula comprises metal peroxides (metal hydroxides or metal hydrides) and aluminum powders (or silica powders); and
wherein weight ratios of metal peroxides or metal hydroxides to aluminum powders range from 1:100 to 100:1.

2. The dressing pack as claimed in claim 1 wherein the inner side of the thin layer can be made of silica gel, nonwovens or plastic breathable film.

3. The dressing pack as claimed in claim 1 wherein the outer side of the thin layer can be made of polypropylene or polyethylene membrane, aluminum coating or composite membrane.

4. The dressing pack as claimed in claim 1 wherein the hydrogen-producing formula or the oxygen-producing formula can be powdered or granulated.

5. The dressing pack as claimed in claim 1 wherein the weight ratios of metal peroxides or metal hydroxides to aluminum powders range from 1:10 to 10:1.

6. The dressing pack as claimed in claim 1 wherein the metal peroxides are selected from a group of metal peroxides consisting of calcium peroxide, magnesium peroxide, sodium peroxide and potassium peroxide.

7. The dressing pack as claimed in claim 1 wherein the metal hydroxides are selected from a group of metal hydroxides consisting of calcium hydroxide, magnesium hydroxide, sodium hydroxide and potassium hydroxide.

8. The dressing pack as claimed in claim 1 wherein the metal hydrides are selected from a group of metal hydrides consisting of magnesium hydride, calcium hydride and silicon hydride.

9. The dressing pack as claimed in claim 1 wherein the hydrogen-producing formula may comprise solid acids which are selected from a group of solid acids consisting of solid citric acid, solid lactic acid, solid oxalic acid, solid hydrochloric acid, solid phytic acid and solid silicic acid for the pH value between 4 and 9.

10. A dressing pack for anti-inflammation, comprising:
a thin layer wrapping a hydrogen-producing formula and an oxygen-producing formula inside, having an airtight outer side as well as an air-permeable inner side on which a plurality of micro pores are opened and featuring a monolayer or a composite layer;
a hydrogen-producing formula wrapped inside the thin layer and not dissipated but absorbing moistures in air or liquid water for generation of hydrogen;
hydrogen permeating a plurality of micro pores and released to skin;
an oxygen-producing formula wrapped inside the thin layer and not dissipated but absorbing moistures in air or liquid water for generation of oxygen;
oxygen permeating a plurality of micro pores and released to skin;
wherein the oxygen-producing formula comprises metal peroxides which are selected from a group of metal peroxides consisting of calcium peroxide, magnesium peroxide, sodium peroxide and potassium peroxide.

11. A dressing pack for anti-inflammation, comprising:
a thin layer wrapping a hydrogen-producing formula and an oxygen-producing formula inside, having an airtight outer side as well as an air-permeable inner side on which a plurality of micro pores are opened and featuring a monolayer or a composite layer;
a hydrogen-producing formula wrapped inside the thin layer and not dissipated but absorbing moistures in air or liquid water for generation of hydrogen;
hydrogen permeating a plurality of micro pores and released to skin;
an oxygen-producing formula wrapped inside the thin layer and not dissipated but absorbing moistures in air or liquid water for generation of oxygen;
oxygen permeating a plurality of micro pores and released to skin;
wherein weight ratios of the oxygen-producing formula to the hydrogen-producing formula range from 1:1 to 1:50.

12. The dressing pack as claimed in claim 1 wherein the inflammation means the non-bacteria inflammation.

\* \* \* \* \*